United States Patent
Kumar

(10) Patent No.: US 12,102,434 B2
(45) Date of Patent: Oct. 1, 2024

(54) SYSTEM FOR ESTIMATING A USER'S RESPONSE TO A STIMULUS

(71) Applicant: ENTROPIK TECHNOLOGIES PRIVATE LIMITED, Karnataka (IN)

(72) Inventor: Ranjan Kumar, Bangalore (IN)

(73) Assignee: ENTROPIK TECHNOLOGIES PRIVATE LIMITED, Bangalore (IN)

( * ) Notice: Subject to any disclaimer, the term of this patent is extended or adjusted under 35 U.S.C. 154(b) by 402 days.

(21) Appl. No.: 17/624,539

(22) PCT Filed: Jul. 2, 2020

(86) PCT No.: PCT/IN2020/050570
§ 371 (c)(1),
(2) Date: Jan. 3, 2022

(87) PCT Pub. No.: WO2021/001851
PCT Pub. Date: Jan. 7, 2021

(65) Prior Publication Data
US 2022/0248996 A1    Aug. 11, 2022

(30) Foreign Application Priority Data
Jul. 2, 2019  (IN) .............................. 201941026450

(51) Int. Cl.
*G06V 40/16* (2022.01)
*A61B 5/00* (2006.01)
(Continued)

(52) U.S. Cl.
CPC .............. *A61B 5/165* (2013.01); *A61B 5/378* (2021.01); *A61B 5/38* (2021.01); *A61B 5/6803* (2013.01);
(Continued)

(58) Field of Classification Search
CPC ........... A61B 5/165; A61B 5/378; A61B 5/38; A61B 5/6803; A61B 5/7267;
(Continued)

(56) References Cited

U.S. PATENT DOCUMENTS

| | | | | |
|---|---|---|---|---|
| 2007/0066916 A1* | 3/2007 | Lemos | ................... | A61B 3/113 |
| | | | | 600/558 |
| 2016/0259492 A1* | 9/2016 | Le | ....................... | G06F 16/9535 |

(Continued)

FOREIGN PATENT DOCUMENTS

| | | | |
|---|---|---|---|
| CN | 107644682 A | | 1/2018 |
| CN | 111108508 A | | 5/2020 |

(Continued)

OTHER PUBLICATIONS

"A novel fuzzy facial expression recognition system based on facial feature extraction from color face images" Engineering Artificial Intelligence vol. 25, Issue 1, Feb. 2012.

(Continued)

*Primary Examiner* — Siamak Harandi
(74) *Attorney, Agent, or Firm* — Maschoff Brennan

(57) ABSTRACT

A method for training a system for measuring or estimating or both of a user's response to a stimulus and for classifying the response is disclosed. The system is trained using a test stimulus presented to one or more users. One or more images of the users' face are captured and simultaneously EEG signals of the users are captured. One or more emotional features are derived from the facial data of the users. One or more cognitive features and emotional features are derived from the EEG signals of each of the users, and a training dataset is created by correlating the one or more emotional features from the facial data, one or more cognitive and emotional features from the EEG signals with one or more features associated with the test stimulus. Created (Continued)

training dataset is used for measuring or estimating or both of a user's response to the stimulus.

11 Claims, 5 Drawing Sheets

(51) Int. Cl.
*A61B 5/16* (2006.01)
*A61B 5/378* (2021.01)
*A61B 5/38* (2021.01)
*G06V 10/764* (2022.01)
*G06V 10/774* (2022.01)
*G06V 10/80* (2022.01)

(52) U.S. Cl.
CPC .......... *A61B 5/7267* (2013.01); *A61B 5/7275* (2013.01); *G06V 10/764* (2022.01); *G06V 10/774* (2022.01); *G06V 10/806* (2022.01); *G06V 40/171* (2022.01); *G06V 40/174* (2022.01); *A61B 2503/12* (2013.01)

(58) Field of Classification Search
CPC .............. A61B 5/7275; A61B 2503/12; G06V 10/764; G06V 10/774; G06V 10/806; G06V 40/171; G06V 40/174; G06F 2203/011; G06F 3/015; G06N 3/044; G06N 3/045; G06N 3/08; G06N 5/01; G06N 20/10; G06N 20/20
See application file for complete search history.

(56) References Cited

U.S. PATENT DOCUMENTS

2018/0060757 A1\* 3/2018 Li .......................... G06N 20/00
2021/0232577 A1\* 7/2021 Ogawa ................. G06V 40/174

FOREIGN PATENT DOCUMENTS

| EP | 1924941 A2 | 5/2008 |
| KR | 20150064977 A | 6/2015 |
| KR | 20200055811 A | 5/2020 |

OTHER PUBLICATIONS

M. Pantic and I. Patras, "Dynamics of facial expression: recognition of facial actions an their temporal segments from face profile image sequences", Apr. 2006.

\* cited by examiner

FIGURE 3

SYSTEM FOR ESTIMATING A USER'S RESPONSE TO A STIMULUS

FIELD OF THE INVENTION

The present disclosure generally relates to artificial intelligence and analysis of mental states, and more particularly relates to a system and method for estimating a user's response to a stimulus.

BACKGROUND TO THE INVENTION

Generally, businesses and researchers across all industries conduct market researches to uncover users' behaviour, thoughts, opinions, interests, etc. about products and services, or to uncover answers to various questions related to market dynamics, business environment and consumer behaviour. There are different types of marketing research classified on the basis of the research objective for which the study is to be carried out and the sources of data used to gather the information. For example, an exploratory research is conducted in cases where the researchers have little or no understanding about the research problem. In another example, a causal research is conducted by the researchers to identify the cause and effect relationship of variables.

Typically, conducting marketing research is time consuming and expensive. However, with the advancement in communication and technology, the market research has evolved from pen and paper surveys, one-on-one interviews, and focus group discussions into something more mobile, instant and convenient. Hence, market research capitalises on the widespread use of devices, such as smartphones, to ask questions, to receive responses, to distribute polls, and to analyse product or service usage. Through such market research, businesses have several ways to improve their content, strengthen their calls to action, and eventually improve conversion rates. Especially, the current consumer and market-oriented economy put a great deal of importance on people's opinions or responses to various visual stimuli such as advertisements, or media. Most of the consumers' exposures to such visual stimuli occur in public places or retail spaces or sometimes in private places (while a user is watching a movie or browsing, etc.) at an immeasurably high number and frequency. The ability to capture such occurrences and take measurements of the responses would provide very valuable information to retailers, marketers, or media content providers. However, capturing such occurrences and responses are difficult and time consuming.

Moreover, for most of the businesses or industries, it is important to analyse or predicts the people's opinions or responses to various visual stimuli such as advertisements, or media prior releasing to the market. For example, for an advertiser, it is important to know and predict the people's opinions or responses to the advertisement before targeting to the audience. However, targeting such an advertisement to a limited set of audience, analysing and predicting people's opinions or responses may not be feasible.

Recent developments in computer vision and artificial intelligence technology make it possible to detect facial expressions and derive the people's behaviour or response based on the facial expressions. However, for predicting the people's opinions or responses to a stimulus, the stimulus needs to be presented to a limited set of audience, for example, the facial expressions needs to measured and analysed to predict response of other people, hence may not be a feasible solution.

SUMMARY OF THE INVENTION

This summary is provided to introduce a selection of concepts in a simple manner that are further described in the detailed description of the disclosure. This summary is not intended to identify key or essential inventive concepts of the subject matter nor is it intended for determining the scope of the disclosure.

The present disclosure discloses a method for training a system for measuring or estimating or both of a user's response to a stimulus and for classifying the response. In one embodiment, the method comprises the steps of, (1) presenting a test stimulus to a one or more users, (2) extracting one or more features associated with the test stimulus and storing in a memory, (3) capturing one or more images of the one or more users' face and simultaneously capturing EEG signals of the one or more users, (4) measuring facial data from the one or more images of each of the one or more users, (5) deriving one or more emotional features from the facial data, and one or more cognitive features and one or more emotional features from the EEG signals of each of the one or more users, (6) creating a training dataset by correlating the one or more emotional features from the facial data, one or more cognitive features and one or more emotional features from the EEG signals with the one or more features associated with the test stimulus, and (7) creating a platform by storing the training dataset, for measuring or estimating or both of a user's response to the stimulus.

Further, a method for measuring or estimating or both of the user's response to the stimulus using the platform is disclosed. In one embodiment, the method comprises, (1) extracting one or more features associated with the stimulus, (2) extracting the one or more features of the test stimulus, stored in the memory associated with the system, that matches with the one or more features of the stimulus, and (3) extracting the one or more of the cognitive features or the one or more emotional features or both from the training dataset matching with the extracted one or more features associated with the stimulus for estimating a user's response to the stimulus and for classifying the response to the stimulus.

To further clarify advantages and features of the present disclosure, a more particular description of the disclosure will be rendered by reference to specific embodiments thereof, which is illustrated in the appended figures. It is to be appreciated that these figures depict only typical embodiments of the disclosure and are therefore not to be considered limiting of its scope. The disclosure will be described and explained with additional specificity and detail with the accompanying figures.

BRIEF DESCRIPTION OF THE FIGURES

The disclosure will be described and explained with additional specificity and detail with the accompanying figures in which:

FIG. 3 illustrates AUs representation on an exemplary image in accordance with an embodiment of the present disclosure.

Figure 1:
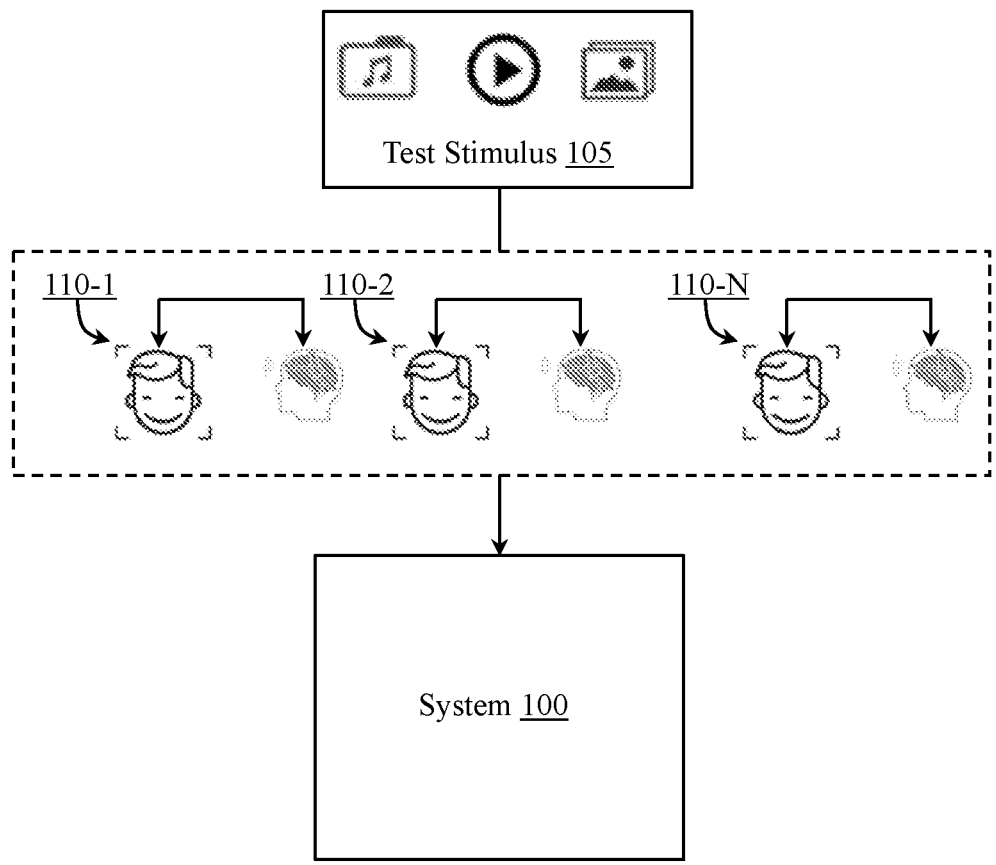
FIG. 1 illustrates an exemplary environment for training a system for measuring or estimating or both of a user's response to a stimulus and for classifying the response in accordance with an embodiment of the present disclosure.

Further, persons skilled in the art to which this disclosure belongs will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those of ordinary skill in the art having benefit of the description herein.

DESCRIPTION OF THE INVENTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications to the disclosure, and such further applications of the principles of the disclosure as described herein being contemplated as would normally occur to one skilled in the art to which the disclosure relates are deemed to be a part of this disclosure.

It will be understood by those skilled in the art that the foregoing general description and the following detailed description are exemplary and explanatory of the disclosure and are not intended to be restrictive thereof.

The terms "comprises", "comprising", or any other variations thereof, are intended to cover a non-exclusive inclusion, such that a process or method that comprises a list of steps does not include only those steps but may include other steps not expressly listed or inherent to such a process or a method. Similarly, one or more devices or sub-systems or elements or structures or components preceded by "comprises . . . a" does not, without more constraints, preclude the existence of other devices, other sub-systems, other elements, other structures, other components, additional devices, additional sub-systems, additional elements, additional structures, or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this disclosure belongs. The system, methods, and examples provided herein are illustrative only and not intended to be limiting.

Embodiments of the present disclosure will be described below in detail with reference to the accompanying figures.

The present disclosure relates to a system and method for measuring or estimating or both of a user's response to a stimulus and for classifying the response. In one embodiment of the present disclosure, the system is trained, that is, one or more training datasets are generated and stored, using a plurality of response collected from the plurality of users to a test stimulus. Then for any given stimulus, the system extracts the one or more features associated with the stimulus and estimates a user response based on the one or more extracted features and the one or more training dataset. The estimated/predicted user response the given/new stimulus is used for classifying the user's response, wherein the classifying the user's response may include predicting general populations response to the new stimulus from a group of responses including, but not limited to, popular, unpopular, one or more measures of popularity or unpopularity, a probability of going viral on social media, a probability of being ignored, one or more measures of comfort, one or more measures of discomfort, one or more measures of anger, one or more measures of revulsion.

FIG. 1 illustrates an exemplary environment for training a system for measuring or estimating or both of a user's response to a stimulus and for classifying the response in accordance with an embodiment of the present disclosure. As shown, in one embodiment of the present disclosure, a test stimulus 105 is presented to a one or more users 110-1 to 110-N (hereafter referred as users 110) and one or more images of the users' 110 face are captured and simultaneously electroencephalogram (EEG) signals are captured, while the users 110 are watching or responding to the test stimulus 105. It is to be noted that the test stimulus 105 is presented to the one or more users 110 using the user device associated with the one or more users, wherein the user device may be one of a smartphone, laptop, PDA, or any such device having or connected with a camera. Further, the EEG signals of the one or more users 110 are captured using EEG headsets. In a preferred embodiment of the present disclosure, a 64 channel EEG headset is used for capturing EEG signal of the one or more users 110 while the one or more users 110 are watching or responding to the test stimulus 105. In one embodiment of the present disclosure, the EEG signals and the one or more images of the one or more users' 110 face are captured along with time stamps. Thus captured one or more images and the EEG signals are stored in a memory associated with the system 100. The test stimulus 105 as described herein may be one of a video, an audio, an image, an advertisement, a promotional content, a web page, a user interface, a chat bot, a mobile app, a video game, and content in any form or format.

The system 100 as described herein may include, for example, a computer server or a network of computers or a virtual server. In one implementation, the system 100 is a cloud server comprising one or more processors, associated processing modules, interfaces and storage devices communicatively interconnected to one another through one or more communication means for communicating information. The storage devices within the system/server 100 may include volatile and non-volatile memory devices for storing information and instructions to be executed by the one or more processors and for storing temporary variables or other intermediate information during processing. It is to be noted that the system 100 may include various other modules such as input/output modules, network interface modules, etc. In one embodiment of the present disclosure, the one or more images of the users' face and the EEG signals of the users 110 may be captured using the user device and the EEG headset worn by the users, and the same may be communicated to the system 100 through a communication network (not shown in FIG. 1).

The communication network as described herein may be a wireless network or a wired network or a combination thereof. Wireless network may include long range wireless radio, wireless personal area network (WPAN), wireless local area network (WLAN), mobile data communications such as 3G, 4G or any other similar technologies. The communication network may be implemented as one of the different types of networks, such as intranet, local area network (LAN), wide area network (WAN), the internet, and the like. The communication network may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like.

Further the communication network may include a variety of network devices, including routers, bridges, servers, modems, computing devices, storage devices, and the like. In one implementation, the communication network is internet which enables communication between the system 100 and user device and the EEG headset worn by the users 110.

As described, in one embodiment of the present disclosure, the EEG signals and the one or more images of the users' 110 face are further processed to derive one or more emotional features and one or more cognitive features in response to the test stimulus. Thus derived one or more emotional features, the one or more cognitive features and one or more features associated with the test stimulus are used for training the system 100 for measuring or estimating or both of a user's response to a stimulus/a stimulus and for classifying the response. The manner in which the system 100 is trained and the system 100 is used for measuring or estimating or both of a user's response to the stimulus is described in detail further below.

Figure 2:
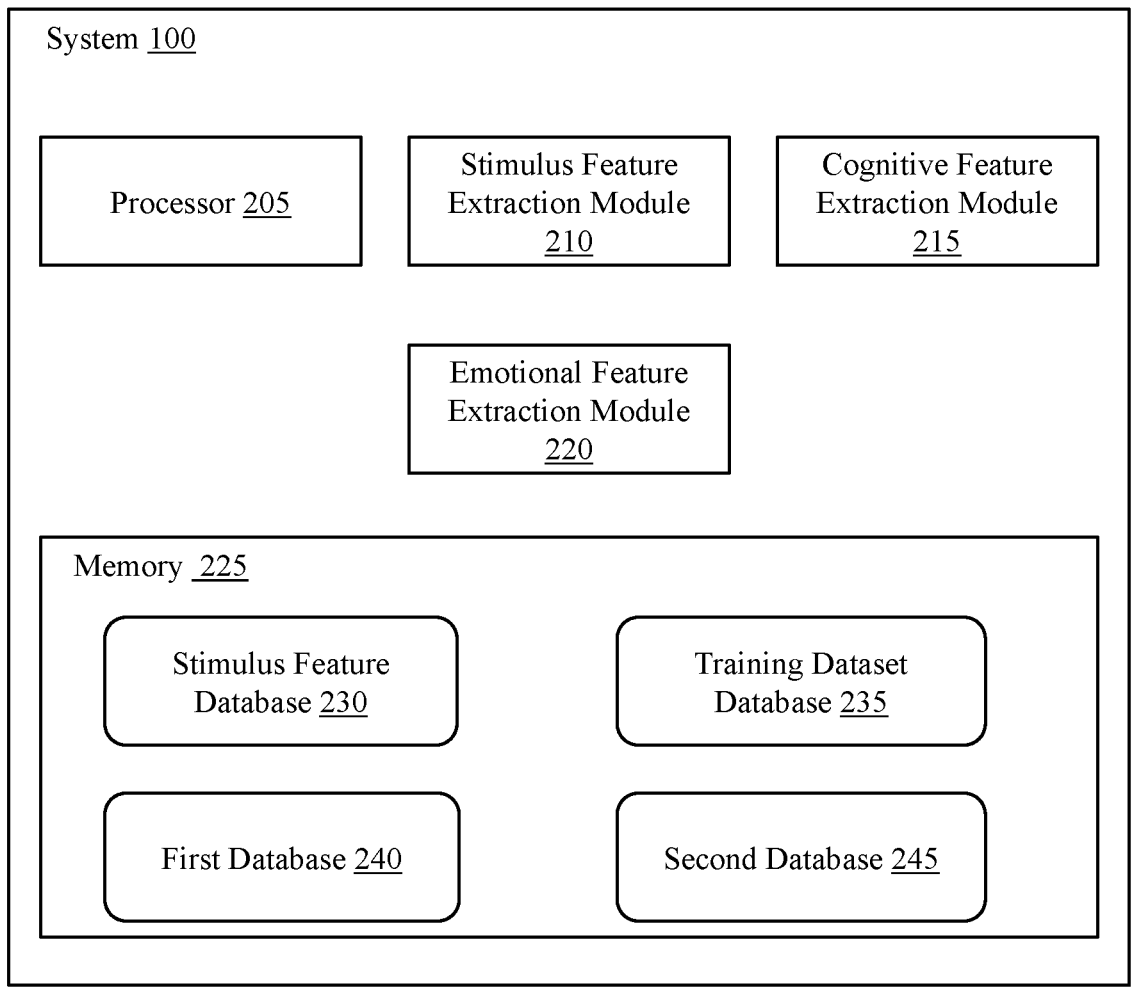
FIG. 2 is a block diagram of the system 100 for measuring or estimating or both of a user's response to the stimulus and for classifying the response in accordance with an embodiment of the present disclosure.

FIG. 2 is a block diagram of the system 100 for measuring or estimating or both of a user's response to the stimulus and for classifying the response in accordance with an embodiment of the present disclosure. In one embodiment of the present disclosure, the system 100 comprises a processor 205, a stimulus feature extraction module 210, a cognitive feature extraction module 215, an emotional feature extraction module 220 and memory 225. The memory 225 further comprises a stimulus feature database 230 for storing one or more features associated with the test stimulus, and a training dataset database 235 for storing a training dataset. The memory 225 may further include a first database 240 for storing a first training dataset and a second database 245 for storing a second training dataset.

As described, a test stimulus 105 is presented to the one or more users 110 and the one or more images of the one or more users' 110 face are captured and simultaneously electroencephalogram (EEG) signals are captured, while the one or more users 110 are watching or responding to the test stimulus 105. In one example, a short video is considered as a test stimulus for ease of description and understanding, and the short video is presented to the one or more users 110 and the one or more images of the one or more users' 110 face are captured and simultaneously electroencephalogram (EEG) signals are captured, while the one or more users 110 are watching the short video. Thus captured responses, that is, the one or more images and the EEG signals are stored in the memory 225 for further processing. In one implementation, the responses are stored along with the timestamps.

In one embodiment of the present disclosure, one or more features of the test stimulus are extracted and stored in the stimulus feature database 230, and one or more emotional features and the one or more cognitive features of the users derived from the responses and are correlated with the one or more features of the test stimulus for training the system for measuring or estimating or both of a user's response to a stimulus and for classifying the response.

Accordingly, in one embodiment of the present disclosure, the stimulus feature extraction module 210 extracts the one or more features of the test stimulus 105, for example one or more features of the short video, and stores in the stimulus feature database 230. The one or more features as described herein may include but not limited to descriptive features, structural descriptive features, segment descriptive features, audio/video features, etc. For example, the one or more features of the short video may include but not limited to video descriptive features such as persons in the video, object activities, subtitles, etc., structural descriptive features such as colour distribution, percentage pixel changes, hue saturation level, optical flow, etc., and segment descriptive features such as shot boundary, scene start and end time, fade-in, fade-out, QoS, resolution, etc. It is to be noted that the one or more features are extracted from the stimulus using any known image, video and/or audio processing technologies and algorithms, for example, linear discriminant analysis, Open-CV, scene detection algorithms, support vector machine (SVM), convolutional neural network (CNN), etc. Further, the one or more features are stored in the stimulus feature database 230 along with the timestamp. For example, for a four minutes video, the one or more features extracted at various times are stored along with the time-stamp.

In one embodiment of the present disclosure, the users' responses to the test stimulus 105, that is, the one or more images of the users' face and the EEG signals are further analysed to derive one or more emotional features and the one or more cognitive features of the response. In a preferred embodiment of the present disclosure, initially a facial data is measured from the one or more images of each of the one or more users and then the one or more emotional features are derived from the facial data. Further, one or more cognitive features and one or more emotional features are derived from the EEG signals of each of the one or more user. Hence, for given test stimulus, perceived emotions are derived from facial data and implicit emotions are derived from the EEG signal associated with each of the one or more users.

In one implementation, the one or more emotional features derived from the one or more images of the users' 110 face using the emotional feature extraction module 220, and the one or more emotional and cognitive features are derived from the EEG signals using the emotional feature extraction module 220 and the cognitive feature extraction module 215 respectively. Hence, the one or more cognitive features such as attention, activation, enjoyment, engagement, etc., and the one or more emotional features such as happy, sad, relax, bore, neutral, etc., towards the given test stimulus (short video) are derived and further correlated with the one or more features associated with the test stimulus using the processor 205, and stored in the training dataset database 235 as the training dataset. In one embodiment of the present disclosure, the one or more emotional and the cognitive features from the EEG signals of the users 110 are extracted using EEG based brainwave mapping.

The manner in which the one or more emotional features are extracted from the one or more images is described in detail further below.

Figure 3:
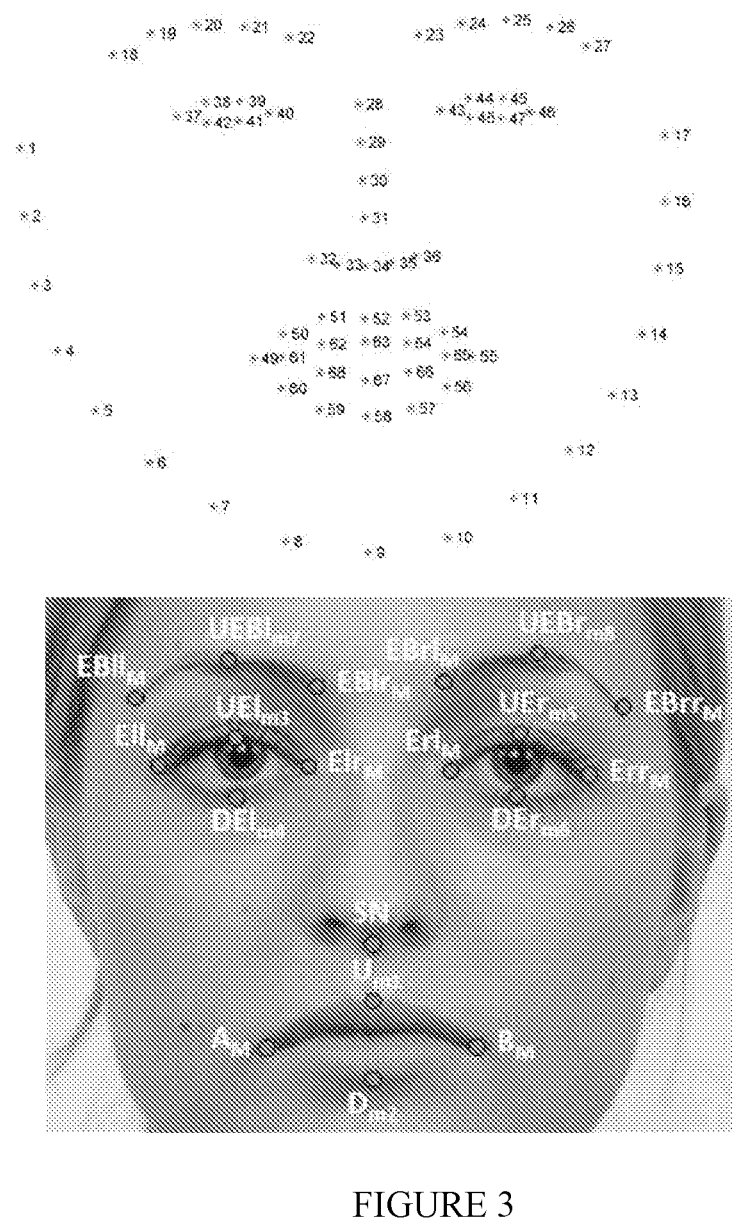

Typically, facial expressions are defined as a combination of different action units (AUs). In other words, combination of different action units defines one or more emotional features (perceived emotions), and the one or more emotional features are derived using the one or more images of the user's face. FIG. 3 illustrates AUs representation on an exemplary image in accordance with an embodiment of the present disclosure. Below table "Table 1" illustrates exemplary AU combination representing different facial expressions.

TABLE 1

| Action Units | Emotion |
| --- | --- |
| 6 + 2 | Happiness |
| 1 + 4 + 15 | Sadness |
| 1 + 2 + 5B + 26 | Surprise |
| 1 + 2 + 4 + 5 + 7 + 20 + 26 | Fear |
| 4 + 5 + 7 + 23 | Anger |
| 9 + 15 + 16 | Disgust |
| R12A + R14A | Contempt |

In one embodiment of the present disclosure, eccentricities of different contours of the user face (plurality of contours of the face) are calculated using different action units or different landmarks. Then, one or more distances and one or more angles between the two or more landmarks are identified and normalized based on the face radius. For example, the distance of nose-edge to the lip corner and many other distances like delta formed between eye-brows and upper nose are calculated and all such distances are normalised by face radius to reduce the effect of differences in faces. Then the one or more emotional features are derived based on the normalized distances. In one embodiment of the present disclosure, a machine learning model is generated using a random forest classifier to derive the one or more emotional features from the one or more images of the user's face.

As described, the training dataset is generated from the users the responses to the test stimulus 105, wherein the training dataset comprises the one or more emotional parameters derived from the facial data of the one or more users 110, and the one or more emotional and the one or more cognitive features derived from the EEG signals of the one or more users in response to the test stimulus. The training dataset further comprises a correlation between the one or more emotional and cognitive features and the one or more features of the test stimulus. Thus generated training dataset is stored in the training dataset database 235, and hence the system 100 provides a platform for measuring or estimating or both of a user's response to the stimulus, that is for any given new stimulus. Hence, the system 100 is trained with plurality of test stimulus of various categories such as video, an audio, an image, an advertisement, a promotional content, a web page, a user interface, a chat bot, a mobile app, a video game, and content in any form or format, and the plurality responses from the plurality of users.

Then the system 100 uses the training dataset (the platform) for measuring or estimating or both of a user's response to a stimulus and for classifying the response. The manner in which the system measures and/or estimates the user's response to a stimulus in described in detail further below.

In one embodiment of the present disclosure, a stimulus, the stimulus for which the users response is to be measured or estimated and the response it to be classified (hereafter referred as new stimulus), is fed to the system 100. It is to be noted that a suitable user interface is provided for inputting the new stimulus to the system 100. Then the stimulus feature extraction module 210 extracts one or more features associated with the new stimulus, wherein the one or more features may include but not limited to descriptive features, structural descriptive features, segment descriptive features, etc. For example, the one or more features of the new short video may include but not limited to video descriptive features such as persons in the video, object activities, subtitles, etc., structural descriptive features such as colour distribution, percentage pixel changes, hue saturation level, optical flow, etc., and segment descriptive features such as shot boundary, scene start and end time, fade-in, fade-out, QoS, resolution etc. It is to be noted that the one or more features are extracted from the stimulus using any known image, video and/or audio processing technologies and algorithms, for example, linear discriminant analysis, Open-CV, scene detection algorithms, support vector machine (SVM), convolutional neural network (CNN), RNN, etc.

Then the processor 205 extracts the one or more features of the test stimulus 105 of similar type, stored in the stimulus feature database 230, which matches with the one or more features of the new stimulus. Then the processor 205 extracting the one or more of the cognitive features or the one or more emotional features or both from the training datasets (stored in training dataset database 235) matching with the extracted one or more features associated with the new stimulus for estimating a user's response to the new stimulus and for classifying the response to the new stimulus. In one example, "Feature A" is extracted from the new stimulus and the one or more cognitive and the one or more emotional features associated with the "Feature A" of the test stimulus is extracted from the training dataset. In one embodiment of the present disclosure, the response to the new stimulus is estimated or measured based on the features of the new stimulus, number and type of responses to the similar feature of the similar test stimulus, etc. In other words, the user's responses to the new stimulus is classified by predicting general populations response to the new stimulus from a group of responses including, but not limited to, popular, unpopular, one or more measures of popularity or unpopularity, a probability of going viral on social media, a probability of being ignored, one or more measures of comfort, one or more measures of discomfort, one or more measures of anger, one or more measures of revulsion. In one embodiment of the present disclosure, the general population response to a new stimulus is predicted based on the one or more emotional and cognitive features derived for the new stimulus.

Figure 4:
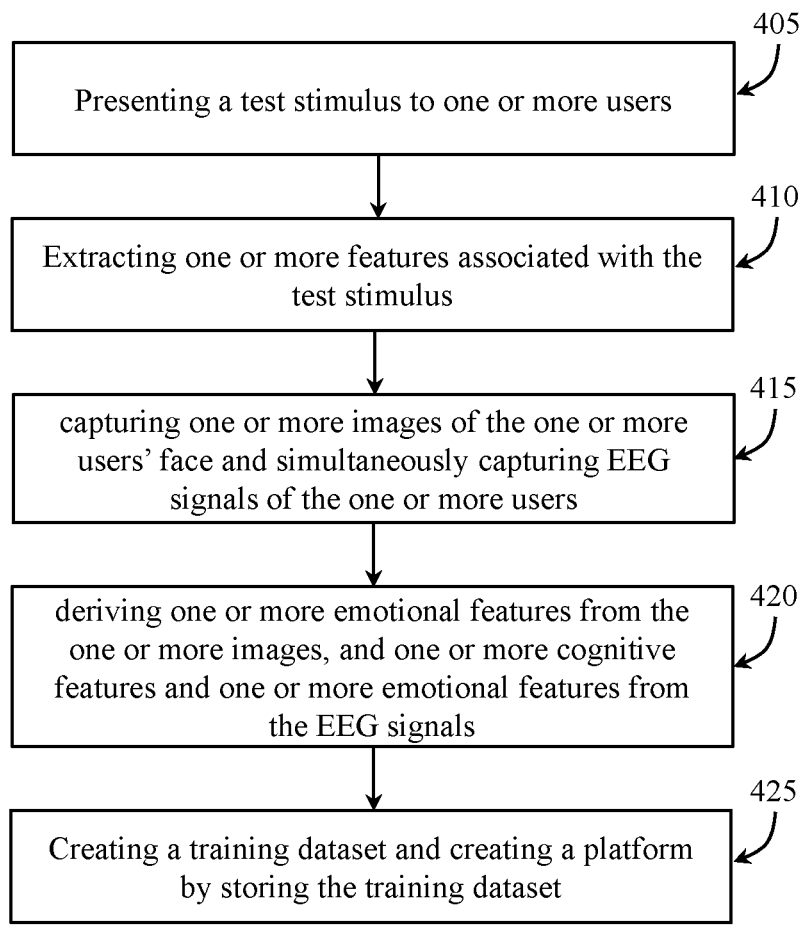
FIG. 4 is a flowchart illustrating a method for training the system 100 for measuring or estimating or both of a user's response to a stimulus and for classifying the response, in accordance with an embodiment of the present disclosure.

FIG. 4 is a flowchart illustrating a method for training the system 100 for measuring or estimating or both of a user's response to a stimulus and for classifying the response, in accordance with an embodiment of the present disclosure.

At step 405, a test stimulus is presented to one or more users, wherein the test stimulus may be one of a video, an audio, an image, an advertisement, a promotional content, a web page, a user interface, a chat bot, a mobile app, a video game, and content in any form or format, and such test stimulus may be presented on the user device associated with the one or more users. As described, the test stimulus may be presented through the Internet.

At step 410, the one or more features associated with the test stimulus are extracted using the stimulus feature extraction module 210 and stored in the stimulus feature database 230, wherein the one or more features may include but not limited to descriptive features, structural descriptive features, segment descriptive features, audio/video features, etc.

At step 415, one or more images of the one or more users' face are captured using the camera associated with the user device and simultaneously EEG signals of the one or more users are captured using EEG headset worn by the users. The one or more images and the EEG signals are captured while the users are watching or experiencing the test stimulus.

At step 420, one or more emotional features are derived from the one or more images, and one or more cognitive features and one or more emotional features from the EEG signals of the users using the emotional feature extraction module 220 and the cognitive feature extraction module 215. In one embodiment of the present disclosure, facial data is derived from the one or more images of each of the one or more users and the one or more emotional features are derived from the facial data. As described, the facial data provides perceived emotions of the users and the EEG signals provide implicit emotions of the users.

At step 425, a training dataset is created by correlating the one or more emotional and cognitive features of the users with the one or more features associated with the test stimulus. The training dataset is stored in the training dataset database 235 for creating a platform for measuring or estimating or both of a user's response to a stimulus and for classifying the response.

Figure 5:
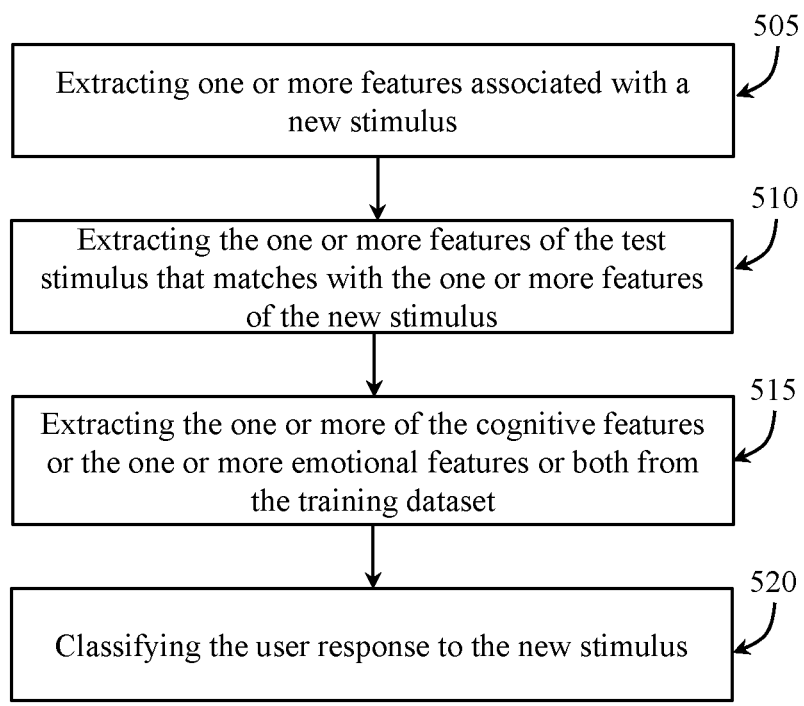
FIG. 5 is a flowchart illustrating a method of measuring or estimating or both of the user's response to a new stimulus using the platform, in accordance with an embodiment of the present disclosure.

FIG. 5 is a flowchart illustrating a method of measuring or estimating or both of the user's response to a new stimulus using the platform, in accordance with an embodiment of the present disclosure.

At step 505, one or more features associated with a new stimulus are extracted using the stimulus feature extraction module 210. The new stimulus may be one of a video, an audio, an image, an advertisement, a promotional content, a web page, a user interface, a chat bot, a mobile app, a video game, and content in any form or format. Further the one or more features associated with the new stimulus may include but not limited to descriptive features, structural descriptive features, segment descriptive features, audio/video features, etc.

At step 510, one or more features of the test stimulus that matches with the one or more features of the new stimulus are extracted from the stimulus feature database 230. For example, considering a video (a new stimulus for which the response is to be measured or estimated), the one or more features of the new video is extracted and one or more features of a test video of similar type are extracted from the stimulus feature database 230 using the processor 205.

At step 515, the one or more of the cognitive features or the one or more emotional features or both matching with the extracted one or more features associated with the stimulus are extracted from the training dataset for estimating a user's response to the stimulus and for classifying the response to the stimulus. Hence, the method and system enables a user or an entity to predict or measure or estimate possible emotional and cognitive response of the users for any new stimulus. Further, the method and system classifies the user's response based on the predicted emotional and cognitive response of the user, historical data associated with the test stimulus, etc. Accordingly, at step 520, the processor 205 classifies the user response to the new stimulus based on predicted or measured or estimated user responses, that is based on emotional and cognitive responses of the user, which are determined based on the training dataset.

Hence, the system and method disclosed in the present disclosure may be implemented for measuring or estimating or both of a user's response to new stimulus, wherein the new stimulus may be one of video, an audio, an image, an advertisement, a promotional content, a web page, a user interface, a chat bot, a mobile app, a video game, and content in any form or format.

Further, the system and method may be used for predicting the response to any given stimulus and hence for advertisement and content optimization, brand benchmarking, for measuring user response before releasing a product or service to the market, for example, before releasing an advertisement, a movie, a mobile application, a webpage or any such content.

In an alternative embodiment of the present disclosure, the training dataset may be further refined for measuring or estimating or both of a user's response to a stimulus and for classifying the response, or for predicting one or more emotional features and one or more cognitive features of a user, given an image of the user's face. In such an implementation, a test stimulus is presented to one or more users, one or more features associated with the test stimulus are extracted and stored in a memory, one or more images of the one or more users' face are captured and simultaneously EEG signals of the one or more users are captured using the EEG headsets, facial data is measured from the one or more images of each of the one or more users, and one or more emotional features are derived from the facial data, and one or more cognitive features and one or more emotional features are derived from the EEG signals of each of the one or more users, as described in the present disclosure with reference to FIG. 1 to FIG. 5.

Then, in one embodiment of the present disclosure, the facial data derived measured from the one or more images of each of the one or more users' face are correlated with the one or more cognitive features and one or more emotional features derived from the EEG signals of the one or more users, and such correlated data is stored in the first database 240 as a first training dataset. For example, considering a short video as a test stimulus, for any given instance, both facial data (one or more images) and EEG signals are captured, and the facial data measured from the one or more images are correlated with the one or more cognitive features and one or more emotional features derived from the EEG signals.

Further, a second dataset is created by correlating the first dataset with the one or more features associated with the test stimulus, and the second dataset is stored in the second database 245. That is, the one or more emotional features and the one or more cognitive features (from the first dataset) are correlated with the one or more features associated with the test stimulus and stores as a second dataset in the second database 245. Hence, the system 100 comprising the first dataset and the second dataset provides a platform for measuring or estimating or both of a user's response to the stimulus or for predicting one or more emotional features and one or more cognitive features of a user.

In one embodiment of the present disclosure, for any new stimulus, initially one or more features associated with the new stimulus are extracted using the stimulus feature extraction module 210. Then, the one or more features of the test stimulus that matches with the one or more features of the new stimulus are extracted from the stimulus feature database 230. Then, the one or more of the cognitive features or the one or more emotional features or both that are matching with the extracted one or more features associated with the stimulus are extracted from the second training dataset for estimating a user's response to the stimulus and for classifying the response to the stimulus as described in the present disclosure.

In another embodiment of the present disclosure, the first training dataset may be used for predicting one or more emotional features and one or more cognitive features of a user, provided one or more images or a video of the user's face. Hence, for predicting one or more emotional features and one or more cognitive features of a user, the system 100 is fed with one or more images of the user's face or a video of the user's face using a dedicated user interface. Then the emotional feature extraction module 220 extracts/measures facial data from the one or more images or from the video as described in the present disclosure. Thus measured facial data of the user is correlated with the first training dataset, and the one or more emotional features and the one or more cognitive features of the user are derived.

Since the data model is trained against the EEG data (brainwave data), that is, the correlation between the emotional features extracted from the facial data and the emotional and cognitive features extracted from the EEG data enhances the emotion prediction accuracy of the system.

Hence the system and method disclosed in the present disclosure may be implemented for measuring or estimating or both of a user's response to a stimulus and for classifying the response or for predicting one or more emotional features and one or more cognitive features of the user.

As described, the system and method may be used for predicting the response to any given stimulus and hence for advertisement and content optimization, brand benchmarking, for measuring user response before releasing a product or service to the market, for example, before releasing an advertisement, a movie, a mobile application, a webpage or any such content.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

I claim:

1. A method for training a system for measuring or estimating or both of a user's response to a stimulus and for classifying the response, the method comprising:
   presenting a test stimulus to a one or more users;
   extracting one or more features associated with the test stimulus and storing in a memory;
   capturing one or more images of the one or more users' face and simultaneously capturing EEG signals of the one or more users;
   measuring facial data from the one or more images of each of the one or more users;
   deriving one or more emotional features from the facial data, and one or more cognitive features and one or more emotional features from the EEG signals of each of the one or more users, wherein deriving the one or more emotional features from the facial data comprises:
      determining eccentricity of a plurality of contours of the face using one or more landmarks;
      calculating distances between the two or more landmarks and normalizing the distances by face radius;
      calculating different angles between the two or more landmarks; and
      deriving the one or more emotional features based on the normalized distances and the distances between the one or more landmarks;
   creating a training dataset by correlating the one or more emotional features from the facial data, one or more cognitive features and one or more emotional features from the EEG signals with the one or more features associated with the test stimulus; and
   creating a platform by storing the training dataset, for measuring or estimating or both of a user's response to the stimulus.

2. A method of measuring or estimating or both of the user's response to the stimulus using the platform of claim 1, method comprising:
   extracting one or more features associated with the stimulus;
   extracting the one or more features of the test stimulus, stored in the memory associated with the system, that matches with the one or more features of the stimulus, and
   extracting the one or more of the cognitive features or the one or more emotional features or both from the training dataset matching with the extracted one or more features associated with the stimulus for estimating a user's response to the stimulus and for classifying the response to the stimulus.

3. The method as claimed in claim 1, wherein the stimulus and the test stimulus is one of a video, an audio, an image, an advertisement, a promotional content, a web page, a user interface, a chat bot, a mobile app, a video game, and content in any form or format.

4. The method as claimed in claim 1, wherein the test stimulus is presented on user devices associated with the first user and the second user.

5. The method as claimed in claim 1, wherein the one or more images of the one or more users' face are captured, using a camera associated with the user devices, while the one or more users are experiencing the test stimulus.

6. The method as claimed in claim 1, wherein the EEG signals of the one or more users are captured, using an EEG headset worn by the one or more users, while the one or more users are experiencing the test stimulus.

7. The method as claimed in claim 1, wherein the facial data comprises facial action units and one or more landmarks.

8. The method of claim 2, wherein the classifying the user's response includes predicting general populations response to the new stimulus from a group of responses including, but not limited to, popular, unpopular, one or more measures of popularity or unpopularity, a probability of going viral on social media, a probability of being ignored, one or more measures of comfort, one or more measures of discomfort, one or more measures of anger, one or more measures of revulsion.

9. A method for training a system for measuring or estimating or both of a user's response to a stimulus and for classifying the response, the method comprising:
- presenting a test stimulus to a one or more users;
- extracting one or more features associated with the test stimulus and storing in a memory;
- capturing one or more images of the one or more users' face and simultaneously capturing EEG signals of the one or more users;
- measuring facial data from the one or more images of each of the one or more users;
- deriving one or more emotional features from the facial data, and one or more cognitive features and one or more emotional features from the EEG signals of each of the one or more users;
- creating a first training dataset by correlating the facial data with the one or more cognitive features and one or more emotional features from the EEG signals;
- creating a second training dataset by correlating the first dataset with the one or more features associated with the test stimulus;
- creating a platform by storing the first and the second training datasets, for measuring or estimating or both of a user's response to the stimulus;
- extracting one or more features associated with the stimulus;
- extracting the one or more features of the test stimulus, stored in the memory associated with the system, that matches with the one or more features of the stimulus; and
- extracting the one or more of the cognitive features or the one or more emotional features or both from the second training dataset matching with the extracted one or more features associated with the stimulus for estimating a user's response to the stimulus and for classifying the response to the stimulus.

10. A method for predicting one or more emotional features and one or more cognitive features of the user using the platform of claim 9, the method comprising:
- receiving one or more images of the user's face or a video of the user's face;
- measuring facial data from the one or more images or from the video;
- deriving the one or more emotional features and the one or more cognitive features of the user by correlating the facial data and the first training dataset.

11. A system for measuring or estimating or both of a user's response to a stimulus and for classifying the response, the system comprising:
- a processor, the processor configured for:
- presenting a test stimulus to a one or more users;
- extracting one or more features associated with the test stimulus;
- capturing one or more images of the one or more users' face and simultaneously capturing EEG signals of the one or more users;
- measuring facial data from the one or more images of each of the one or more users;
- deriving one or more emotional features from the facial data, and one or more cognitive features and one or more emotional features from the EEG signals of each of the one or more users;
- creating a training dataset by correlating the one or more emotional features from the facial data, one or more cognitive features and one or more emotional features from the EEG signals with the one or more features associated with the test stimulus; and
- creating a platform by storing the training dataset, for measuring or estimating or both of a user's response to the stimulus;
- a memory, the memory configured for:
- storing one or more features associated with the test stimulus;
- storing training dataset;
- wherein, the processor is further configured for:
- extracting one or more features associated with the stimulus;
- extracting the one or more features of the test stimulus, stored in the memory associated with the system, that matches with the one or more features of the stimulus, and
- extracting the one or more of the cognitive features or the one or more emotional features or both from the training dataset matching with the extracted one or more features associated with the stimulus for estimating a user's response to the stimulus and for classifying the response to the stimulus.

* * * * *